United States Patent [19]

Shah et al.

[11] Patent Number: 5,519,127
[45] Date of Patent: May 21, 1996

[54] NUCLEIC ACID PROBES FOR THE DETECTION OF *PNEUMOCYSTIS CARINII*

[75] Inventors: Jyotsna Shah, Nashua, N.H.; Amelia Buharin, Roslindale; David J. Lane, Milford, both of Mass.

[73] Assignee: Amoco Corporation, Naperville, Ill.

[21] Appl. No.: 826,657

[22] Filed: Jan. 21, 1992

Related U.S. Application Data

[63] Continuation-in-part of Ser. No. 392,679, Aug. 11, 1989, abandoned.

[51] Int. Cl.$^6$ ..................................................... C07H 21/00
[52] U.S. Cl. ..................... 536/24.32; 536/23.1; 536/24.3
[58] Field of Search ................................. 536/27, 28, 29, 536/23.1, 24.3, 24.32

[56] References Cited

U.S. PATENT DOCUMENTS

| | | | |
|---|---|---|---|
| 4,801,536 | 1/1989 | Stahl et al. | 435/68 |
| 4,851,330 | 7/1989 | Kohne | 435/6 |
| 4,857,637 | 8/1989 | Hammonds et al. | 530/403 |

OTHER PUBLICATIONS

L. Medlin et al., "The characterization of enzymatically amplified eukaryotic 16S–Like rRNA–coding regions", Gene, vol. 71, 1988, pp. 491–499.

S. L. Stringer et al., "*Pneumocystis carinii*: Sequence from Ribosomal RNA Implies a Close Relationship with Fungi", Experimental Parasitology, vol. 68, 1989, pp. 45–461.

K. Tanabe et al., "Use of *Pneumocystis carinii* Genomic DNA Clones for DNA Hybridization Analysis of Infected Human Lungs", The Journal of Infectious Diseases, vol. 157, No. 3, 1988, pp. 593–596.

J. C. Edman et al., "Ribosomal RNA sequence shows Pneumocystis carinii to be a member of the Fungi", Nature, vol. 334, 1988, pp. 519–522.

Nature, vol. 334, pp. 519–522, Aug. 11, 1988.

Imajoh et al., Biochemistry, vol. 27, pp. 8122–8128 (1988).

Kirchgessner et al., J. of Biol. Chem., vol. 262, No. 18, pp. 8463–8469, Jun. 25, 1987.

Micheals et al., Eur. J. of Biol., vol. 166, pp. 55–61, Jul. 1, 1987.

*Primary Examiner*—Douglas W. Robinson
*Assistant Examiner*—James O. Wilson
*Attorney, Agent, or Firm*—Norval B. Galloway

[57] ABSTRACT

Nucleic acid probes capable of hybridizing to rRNA or rDNA of *Pneumocystis carinii* and not to rRNA or rDNA of non-Pneumocystis are described along with methods utilizing such probes for the detection of *Pneumocystis carinii* in clinical samples.

12 Claims, No Drawings

5,519,127

NUCLEIC ACID PROBES FOR THE DETECTION OF *PNEUMOCYSTIS CARINII*

This is a continuation-in-part of application Ser. No. 07/392,679, filed Aug. 11, 1989, now abandoned.

FIELD OF THE INVENTION

This invention relates to detecting fungi belonging to the species *Pneumocystis carinii* and more specifically provides nucleic acid probes and compositions along with methods for their use for the specific detection of *Pneumocystis carinii*.

BACKGROUND OF THE INVENTION

The term "*pneumocystis carinii*" as used herein, refers to fungus classified as such by a method for phylogenetic grouping based upon the sequences of small subunit rRNA (Edman J. C., Kovacs, J. A., Masur, H., Santi, D. V., Elwood, H. J. and Sogin, M. L. [1988] Nature, 334:519). *Pneumocystis carinii* is a member of the genus Pneumocystis. *Pneumocystis carinii* is an opportunistic lower respiratory tract pathogen. It is a small unicellular organism and is believed to exist in the mammalian host in two basic forms: the trophozoite and the cyst.

*Pneumocystis carinii* infects humans and most mammalian host. Although the parasite rarely causes illness in normal individuals, it characteristically gives rise to life threatening interstitial pneumonia in certain conditions of immunodeficiency and is one of the most common causes of morbidity and mortality in acquired immune deficiency syndrome.

Current means of diagnosis of Pneumocystis pneumonia include the use of histological techniques, such as Gomori's methenamine silver, Toludine Blue or Giemsa stains, on respiratory tract samples such as Bronchoalveolar lavage sample or, more commonly, induced sputum samples. These staining procedures require the specialist expertise of a cytologist to interpret the results. A number of rapid laboratory methods recently have become available. Some of them are antibody-based tests whereas others are DNA based tests. It is an aspect of the present invention to provide nucleic acid probes which are specific for Pneumocystis and which do not react with other fungi and bacteria which may be present in sampled materials. Such probes may be used in a variety of assay systems which avoid many of the disadvantages associated with the traditional methods.

It is another aspect of the present invention to provide probes which can hybridize to target regions which can be rendered accessible to probes under normal assay conditions.

While Kohne et al. (Biophysical Journal 8:1104–1118, 1968) discuss one method for preparing probes to rRNA sequences, they do not provide the teaching necessary to make *Pneumocystis carinii* specific probes.

Pace and Campbell (Journal of Bacteriology 107:543–547, 1971) discuss the homology of ribosomal ribonucleic acids from diverse bacterial species and a hybridization method for quantitating such homology levels. Similarly, Sogin, Sogin and Woese (Journal of Molecular Evolution 1:173–184, 1972) discuss the theoretical and practical aspects of using primary structural characterization of different ribosomal RNA molecules for evaluating phylogenetic relationships. Fox, Pechman and Woese (International Journal of Systematic Bacteriology 27:44–57, 1977) discuss the comparative cataloging of 16S ribosomal RNAs as an approach to procaryotic systematics. These references, however, fail to relieve the deficiency of Kohne's teaching with respect to fungus and in particular to human *Pneumocystis carinii* and do not provide *Pneumocystis carinii* specific probes useful in assays for detecting *Pneumocystis carinii* in clinical samples.

Hogan et al. (European patent publication WO 88/03957) describe a number of probes which are claimed to hybridize to a broad representation of eubacteria and fungi. However, Hogan et al. do not disclose the probes of the present invention, nor do they provide the teaching necessary to design such probes.

Edman, Kovacs, Masur, Santi, Elwood and Sogin (Nature, 334, pp. 519–522, 1988) describe a set of three probes to the 18S rRNA of the rat Pneumocystis. There is no known correlation between rat Pneumocystis and human Pneumocystis infections since it is not known whether rat Pneumocystis can cause the human disease. Edman et al. do not disclose the human Pneumocystis probes or the ferret Pneumocystis probes of the present invention, nor do they provide the teaching necessary to design such probes.

Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain four distinct RNA molecules which, at least in *Saccharomyces cerevisiae*, are referred to as 5S, 5.8S, 18S and 28S rRNAs. These names historically are related to the size of the RNA molecules, as determined by their sedimentation rate. In actuality, however, ribosomal RNA molecules vary substantially in size between organisms. Nonetheless, 5S, 5.8S, 18S, and 28S rRNA are commonly used as generic names for the homologous RNA molecules in any eubacterial cell and this convention will be continued herein.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially, see below—Hybridization) to target nucleic acid sequences. In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluorescien, 32-P, biotin, etc.), or to facilitate their capture onto a solid support (e.g., poly-deoxyadenosine "tails"). Such modifications are elaborations on the basic probe function which is its ability to usefully discriminate between target and non-target organisms in a hybridization assay.

Hybridization traditionally is understood as the process by which, under predetermined reaction conditions, two partially or completely complementary strands of nucleic acid are allowed to come together in an antiparallel fashion to form a double-stranded nucleic acid with specific and stable hydrogen bonds.

The stringency of a particular set of hybridization conditions is defined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art. As a general matter, dependent upon probe length, such persons understand stringent conditions to mean approximately 35° C.–65° C. in a salt solution of approximately 0.9 molar.

SUMMARY OF THE INVENTION

In accordance with the various principles and aspects of the present invention, there are provided nucleic acid probes and probe sets comprising DNA or RNA sequences which hybridize, under specific conditions, to the ribosomal RNA molecules (rRNA) or rRNA genes (rDNA) of *Pneumocystis carinii* but which do not hybridize, under the same conditions, to the rRNA or rDNA of other fungi and bacteria which may be present in test samples. Therefore the probe(s) of the present invention provide the basis for development of a valuable nucleic acid hybridization assay for the specific detection of *Pneumocystis carinii* in clinical samples.

In our experience such nucleic acid hybridization based assays have been discovered to impart enhanced performance capabilities with respect to most currently available, microbiological methods for detection of bacteria and fungus in test samples, generally including:

a) increased sensitivity; i.e., the ability to detect said bacteria or fungus in a given sample more frequently;

b) potentially significant reductions in assay cost due to the use of inexpensive reagents and reduced labor;

c) accurate identification of even biochemically unusual strains of the target bacteria or fungus;

d) faster results because such tests do not require the isolation of the target bacterium or fungus from the sample prior to testing.

It has been discovered that other advantages incurred by directing the probes of the present invention against rRNA include the fact that the rRNAs detected constitute a significant component of cellular mass. Although estimates of cellular ribosome content vary, actively growing *Pneumocystis carinii* may contain upwards of 50,000 ribosomes per cell, and therefore 50,000 copies of each of the rRNAs (present in a 1:1:1:1 stoichiometry in ribosomes). In contrast, other potential cellular target molecules such as genes or RNA transcripts thereof, are less ideal since they are present in much lower abundance.

A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides probes to *Pneumocystis carinii* rRNA target sequences which are sufficiently similar in all *Pneumocystis carinii* human isolates tested so far that they can hybridize to the target region in all such human *Pneumocystis carinii*. Advantageously, these same rRNA target sequences are sufficiently different in most non-human *Pneumocystis carinii* rRNAs that, under conditions where probes 1485 and 1487 hybridize to human *Pneumocystis carinii* rRNAs, they do not hybridize to most non-human Pneumocystis rRNAs. These probe characteristics are defined as inclusivity and exclusivity, respectively.

The other probes of the present invention, probes 1159, 1162, 1484, 1486, 1488, 1491, 1492, are as inclusive for all the human *Pneumocystis carinii* isolates tested as probes 1485 and 1487, and, in addition, these probes also hybridize to non-human *Pneumocystis carinii*. Probes 1493, 1494, 1495 hybrize to ferret *Pneumocystis cariniis* and not to human *Pneumocystis carinii*. Probe 1159 also hybridizes to other fungi is a useful component of probe sets which may be particularly useful in certain assay formats. It is not clear at the present time whether *Pneumocystis carinii* from non-human sources can also infect humans so all of the above probes will be useful, at least initially in research assays.

The discovery that probes could be generated with the extraordinary inclusivity and exclusivity characteristics of those of the present invention with respect to *Pneumocystis carinii* was unpredictable and unexpected.

BRIEF DESCRIPTION OF THE TABLES

Further understanding of the principles and aspects of the present invention may be made by reference to the tables wherein:

Table 1—Shows the nucleotide sequences of the preferred 18S rRNA-targeted probes of the present invention aligned upon their *Pneumocystis carinii* target nucleotide sequences. The corresponding portions of the 18S rRNA from *Saccharomyces cerevisiae* is shown for comparison. RNA (target) sequences are written 5' to 3', probe sequences are DNA and written 3' to 5'. Probes are shown along with the "core" region of variation upon which their inclusivity and exclusivity behavior are based.

Table 2—Exemplifies the inclusivity behavior of the preferred 18S rRNA probes toward a representative sampling of DNA and RNA preparations from *Pneumocystis carinii* strains in dot blot-hybridization assay.

Table 3—Exemplifies the exclusivity behavior of the preferred 18S rRNA probes toward a representative sampling of non- *Pneumocystis carinii* fungi and bacteria in a dot blot hybridization assay.

DETAILED DESCRIPTION OF THE INVENTION AND BEST MODE

Probe Development Strategy

The first step taken in the development of the probes of the present invention involved identification of regions of 18S rRNA which potentially could serve as target sites for *Pneumocystis carlnil* specific nucleic acid probes. As a practical matter, it is difficult to predict, a priori, which non-*Pneumocystis carinii* organisms might be present in any test sample.

Because of the large number of such potential non-*Pneumocystis carinii* fungi and bacteria, demonstrating exclusivity for any given probe sequence is not only unpredictable but also extremely difficult and laborious. A more rigorous criterion was adopted to obviate the need to know what non-Pneumocystis fungus and bacteria might be present in all test samples that ultimately will be screened using the probes.

This entailed knowledge of the phylogenetic relationships among *Pneumocystis carinii* and between *Pneumocystis carinii* and other fungi. Specifically, an operating but previously unproven hypothesis was adopted that the exclusivity criterion could be satisfied by determining that if a particular target region in *Pneumocystis carinii* rRNA could be identified which was sufficiently different from the homologous region in the rRNA of representative yet close evolutionary relatives of *Pneumocystis carinii*, then a probe to such a sequence could be used to distinguish between *Pneumocystis carinii* and the relatives by hybridization assay. Based on phylogenetic observations, it then was extrapolated that rRNA sequences of more distantly related organisms, even though their actual identity may not necessarily be known, should be predictably different in a particular region of sequence than the aforementioned close evolutionary relative of *Pneumocystis carinii*. However, it cannot be predicted, a priori, whether such regions exist or if they do, where within the rRNA such regions will be located.

As the first step in identifying regions of *Pneumocystis carinii* rRNA which could potentially serve as useful target sites for nucleic acid hybridization probes, nucleotide sequences of the 18S rRNA from several representative *Pneumocystis carinii* was determined.

Coding regions of 18S rRNA genes of *Pneumocystis carinii* were amplified by polymerase chain reaction (U.S. Pat. No. 4,683,202) from about 0.5 to 1.0 ug of total DNA, of *Pneumocystis carinii* infected human or ferret lung tissues using primers 936 (forward primer) and 935 (reverse primer). Primer 936 is designed to hybridize to the 18S rDNA gene strand complimentary to the fungal 18S rRNA. Primer 935 hybridizes to the rRNA-like strand of the 18S ribosomal RNA gene. The amplified 18S rRNA genes were cloned by standard laboratory protocols (Manjarls et al., 1982, Molecular Cloning; A Laboratory Manual, Cold Spring Harbor Laboratory, New York, pp. 545) using restriction endonuclease sites designed into the primers. Sequencing was performed by the method of Sanger et al., 1977, Proceedings of the National Academy of Science, USA 74:5463–5467.

The determined *Pneumocystis carinii* rRNA nucleotide sequences were compared to other available rRNA nucleotide sequences, in particular to *Saccharomyces cerevisiae*.

Comparison of the sequences of different host specific *Pneumocystis carinii* and its close relative *Saccharomyces cerevisiae* proved especially valuable. Several regions of sequence were identified which appeared to be different in the different host specific *Pneumocystis carinii* and between and non-Pneumocystis fungus. The locations of these regions within the 18S rRNA sequences are shown in Table 1.

In the context of the objectives of the present invention, oligonucleotide probes, 33–48 nucleotides in length, were designed which would hybridize preferentially to human or rat or ferret *Pneumocystis carinii* or all three. These were designed: 1) to maximally utilize the nucleotide sequence differences useful for distinguishing *Pneumocystis carinii* from *Saccharomyces cerevisiae* or Pneumocystis from other fungus [indicated as upper case letters in the region of Core Variation, Table 1] and 2) to minimize the effect of self complementarity both locally within the target rRNA and between probe molecules. Optimizing these parameters as well as others discussed above (BACKGROUND) results in probes of preferred specificity and hybridization efficiency.

Table 2 exemplifies the inclusivity behavior of the preferred probes toward a representative sampling of *Pneumocystis carinii* by Southern blot hybridization assay.

Table 3 exemplifies the exclusivity behavior of the preferred probes toward a representative sampling of non-*Pneumocystis carinii* fungi and bacteria in a dot-blot hybridization assay.

Physical Description of the Probes

The foregoing probe selection strategy yielded a number of probes useful for identifying *Pneumocystis carinii* in clinical samples. All the probes 1159, 1162, 1484, 1485, 1486, 1487, 1488, 1491, 1492, 1493, 1494, 1495, 1496 and 1497 are designed from 18S rRNA sequences. The following preferred oligonucleotide probes are disclosed herein:

18S rRNA-Targeted Probes:

Probe 1159: 5'-cTATTCGAGCAAACGCCTGCTTTGAA-CACTCTAATTTTCTCAAAGTcT

Probe 1162: 5'-cAAGAAGCCCGCGATCAG-CAAAAGCTAATCTGGCTATTTcT

Probe 1484: 5'-cGCACACACTTCGGAGGACCGGGC-CGTCAACCCC-3'

Probe 1485: 5'-cGAAGGGCATACCGGTAATCCAGAAG-GAAGGATC-3'

Probe 1486:5'-cTAAGAAGCCTGCGATCAG-CAAAAGCTAATCTGC-3'

Probe 1487: 5'-cGTCATCGTTGCCAACAGCCCGCTGC-CAGTCCGAA-3'

Probe 1488: 5'-cAATGACCAAATTTGATCAACTTTC-CAGCAATGG-3'

Probe 1491:5'-cAATGACCAAATTTGATCAACTTTC-CAGCAACAG-3'

Probe 1492: 5'-cTAAGAAGCCTGCGATCAGCGAAT-GCTAATCTGG-3'

Probe 1493:5'-cCACACCTTTCCGGAGGACCGGG-TAACCAATCCC-3'

Probe 1494:5'-cGAACATCGAAACCAATGACCATTAC-CGGTCCGAA-3'

Probe 1495:5'-cGCCATCGTTACCAATGGCCCATCGC-CAGTCCGAA-3'

Probe 1496:5'-cGAAGGGCATGCTGGTAAATCCAG-GAAGAAGGGTC-3'

Probe 1497: 5'-cGAAGAGCATATTGGTAATCCAGAAG-GAAGGATC-3'

The probes and their target sequences in the 18S rRNAs of *Pneumocystis carinii* are shown in Table 1. The corresponding nucleotide positions of the *Saccharomyces cerevisiae* 18S rRNA also are shown.

In addition, two oligonucleotide primers 935 and 936 were designed for the PCR amplification of Pneumocystis 18S rRNA genes in order to facilitate the analysis of these genes in these non-culturable organisms. These two primers are described by L. Medlin, H. L. Elwood, S. S. Stickel and M. L. Sogin (Gene 71:491–499, 1988). The sequences of these primers are given below or clarity of presentation.

Primer 936: 5'-ccgaattcgtcgacaacCTGGTTGATC-CTGCCAGT-3'

Primer 935: 5'-cccgggatccaagctTGATCCTTCTG-CAGGTTCACCTAC-3'

For primers 935 and 936 the portions in lower case letters are designed to add useful restriction endonuclease recognition cloning sites to the amplified products. The portions in upper case letters correspond to the nucleotides which hybridize specifically to the 5' (primer 936) or 3' (primer 935) ends of the 18S rRNA gene.

More than one probe has been designed to a number of the target regions shown in Table 1 corresponding variously to 1) complements of the sequences of different isolates of *Pneumocystis carinii* where such isolates exhibit several sequence differences, or 2) to those of all *Pneumocystis carinii* where little or no sequence variations among *Pneumocystis carinii* isolates was found. The particular sequence upon which each probe is based (i.e., is complementary to)

is provided in Table 1 by inspection of the aligned probe and target sequences. Thus, for example, it can be seen in Table 1 that probe 1484 is complementary to the human *Pneumocystis carinii* sequence through this target region and the related probe 1493 is complementary to the ferret *Pneumocystis carinii* sequence. (Base pairing rules dictate that A pairs with T or U and G pairs with C, although various non canonical base pairs to a first approximation [i.e. G:U, G:T or A:G] can be introduced into the probe for specific purposes.) However, it is expected (and desirable) that some cross-hybridization between *Pneumocystis carinii* strains by one or both probes will take place.

The specific hybridization behaviors of the probes described above are dependent to a significant extent on the assay format in which they are employed. Conversely, the assay format will dictate certain of the optimal design features of particular probes. The "essence" of the probes of the invention is not to be construed as restricted to the specific string of nucleotides in the probes named above. For example, the length of these particular oligonucleotides was optimized for use in the dot blot assay (and certain other anticipated assays) described below. It is well known to one skilled in the art that optimal probe length will be a function of the stringency of the hybridization conditions chosen and hence the length of the instant probes may be altered in accordance therewith. Also, in considering sets comprised of more than one probe, it is desirable that all probes behave in a compatible manner in any particular format in which they are both employed. Thus, the exact length of a particular probe will to a certain extent reflect its specific intended use.

The "essence" of the probes described herein resides in the discovery and utilization of the *Pneumocystis carinii* specific sequences described above and given in Table 1 (Core Variation).

The invention does not only cover the above-described probes (e.g., probe 1485, probe 1487, or probe 1159), it also includes nucleic acid fragments which contains a shorter segment of the disclosed probes. Such nucleic acid fragments can also be used as probes for detection of specific *Pneumocystis carinii*.

The method of selecting a shorter segment from the above-disclosed probes for preparation of probes is well known in the art. Take probe 1485 as an example. The alignment of probe 1485 and its corresponding sequence from rat *Pneumocystis carinii* is as follows.

```
GATCCTT—CCTTCTGGATTACCGGT ATGCCCTTC   (probe 1485)
|||||||  ||| ||||||||||||    |||||||||
GATCCTTC CCTCCTGGATTACCGG—CTGCCCTTC   (rat P. c.)
```

Two preferred 15-base nucleic acid segments from probe 1485 are TCCTTCCTTCTGGAT and TACCGGTATGCCCTT, since each of them aligns with its corresponding rat *Pneumocystis carinii* sequence in such a manner (see below) that the mismatches have maximal effect in enabling the 15-base segments to distinguish *Pneumocystis carinii* sequences from human and rat in a hybridization assay.

```
TCCTT—CCTTCTGGAT
|||||  ||| |||||||
TCCTTC CCTCCTGGAT

TACCGGT ATGCCCTT
||||||   |||||||
TACCGG—CTGCCCTT
```

Hybridization Analysis of Probe Behavior.

The sequence data in Table 1 suggests that the probes of the present invention should exhibit a variety of useful hybridization properties with respect to the specific detection of *Pneumocystis carinii* to the exclusion of other fungi and bacteria. However, relatively few *Pneumocystis carinii* sequences were inspected. It is possible that sequence variation might exist in other *Pneumocystis carinii* not inspected by sequence analysis. Such variation might reduce or eliminate hybridization by the prospective probes to such untested *Pneumocystis carinii* isolates.

Equally as important as the inclusivity behavior of the probes, is their exclusivity behavior, i.e., their reactivity toward non-Pneumocystis fungi and bacteria. The number and types of non-*Pneumocystis carinii* strains which might be encountered in a potentially Pneumocystis containing test sample are extremely large.

Therefore, the behavior of the probes toward representative *Pneumocystis carinii* and non-*Pneumocystis carinii* fungi and bacteria was determined by hybridization analysis using dot blot procedures.

While hybridization data for each of the individual probes of the present invention are provided, it should be noted that useful combinations (sets) of probes which exhibit hybridization behaviors that are the sum of the individual probes also are explicitly predicted by the data.

EXAMPLE 1

Southern blot analysis of probe hybridization behavior.

Southern blot analysis, in accordance with well known procedures, involves size fractionating DNA on acrylamide or agarose gels, denaturing the DNA in the gels and then transferring and immobilizing the DNA from the gel onto a filter such as nitrocellulose, nylon, or other derivatized membranes (which readily can be obtained commercially, specifically for this purpose) either by electrophoresis or capillary action (i.e "blotting"). DNA is subsequently probed or tested for hybridization under any of a variety of conditions (i.e., stringencies) with nucleotide sequences or probes of interest. Under stringent conditions, probes whose nucleotide sequences have greater complementarity to the target sequence will exhibit a higher level of hybridization than probes containing less complementarity.

For the experiment shown in Table 2, DNA was extracted from bronchial lavage or induced sputum samples of *Pneumocystis carinii* positive (human) patients by standard methods. 18S rDNA genes of *Pneumocystis carinii* from about 0.5 to 1.0 ug of total DNA were amplified using 18S rRNA-specific primers 935 (forward primer) and 936 (reverse primer) by polymerase chain reaction (PCR) (U.S. Pat. No. 4,683,202). One tenth of the PCR material was run on a 1% agarose gel, transferred onto a nitrocellulose membrane as described by Southern (Maniatis Cloning Manual). P-32 end-labeled oligonucleotide probes then were hybridized to the filters.

For the oligonucleotide probes described herein, hybridization to rDNA targets was done at 60° C. for 14–16 hours (in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidine), followed by three 15 minute post-hybridization washes at 60° C. (in 0.03M NaCl, 0.004M Tris-HCl, pH 7.8, 0.2 mM EDTA, and 0.1% SDS) to remove unbound probes.

Following hybridization and washing as described above, the hybridization filters were exposed to X-ray film and the intensity of the signal was "scored" visually with respect to control lanes of known amount of target material (DNA). A scale of hybridization intensity ranging from ++++ (hybridization signal equivalent to that of control *Pneumocystis carinii* lane for which a perfect match between probe and target sequences has been explicitly determined by sequence analysis) to + (barely detectable even after long exposure of X-ray film) or (no hybridization) has been used to conveniently compare hybridization signals between different organisms and the probes. This reporting format is preferred to raw numerical representation of the extent of hybridization as it permits ready visual scanning of the summary data.

As is evident in Table 2, probes 1159, 1162, 1484, 1486, 1488, 1491 and 1492 hybridize to the amplified 16S ribosomal RNA genes and RNA of all the *Pneumocystis carinii* isolates tested. The rest of the probes hybridize to different host specific *Pneumocystis carinii* in varying potentially useful patterns.

EXAMPLE 2

Dot blot analysis of probe hybridization behavior.

Dot blot analysis, in accordance with well known procedures, involves immobilizing a nucleic acid or a population of nucleic acids on a filter such as nitrocellulose, nylon, or other derivatized membranes which readily can be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Under stringent conditions, probes whose nucleotide sequences have greater complementarity to the target sequence will exhibit a higher level of hybridization than probes containing less complementarity.

For the experiment shown in Table 3, one tenth of a microgram of purified RNA (Lane et al., 1985, Proceedings of the National Academy of Science, USA 82:6955–6959) from each of the indicated organisms was spotted on nitrocellulose filters. The oligonucleotide probes were end-labeled with radioactive phosphorous 32 using standard procedures.

Hybridization of the oligonucleotide probes to rRNA in the dots was as described in Example 1.

Following hybridization and washing the hybridization filters were exposed to X-ray film and the intensity of the signal "scored" visually with respect to control spots of known amount of target material (RNA) as described above (Example 1).

As indicated in Table 3, all the probes except 1159 appear to have excellent exclusivity behavior (i.e., hybridization to *Pneumocystis carinii* [Table 2] but not to any other fungus or bacteria). Probe 1159 has broader inclusivity than the rest of the probes. In addition to hybridizing to all the *Pneumocystis carinii* isolates tested, it hybridizes to several other fungi as well as to mammalian rRNA (to varying degree). Probe 1159 is designed as a "companion" detection ligand-carrying probe and is useful when used in conjunction with the Pneumocystis-specific probes described herein in dual probes hybridization formats such as that described in Example 4 below.

EXAMPLE 3

Inclusivity Analysis of probe hybridization behavior in in-situ hybridization assay.

In-situ nucleic acid hybridization with isotopically or fluorescently labeled probes is widely used for the intracellular localization and quantitation of RNAs and genes (Gall J. G. and Pardue M. L. [1969]Proc. Natl. Acad. Sci. USA 63:378; Brigati, D., Myerson, Leary, J. J., Spalholz B., Travis, S. Z., Fong, C. K. Y., Hsiung, G. D., and Ward, D. C. [1983] Virology 126:32; Cox, K. C., Deleon, D. V., Angerer, L. M., and Angerer, R. C., [1984] Devel. Biol. 101: 485; Lawrence, J. B., Viiinave, C. A., and Singer, R. H., [1988] Cell 52:51; Delong, E. F., Wickham, G. S., and Pace, N. R., [1989] Science 243:1360). Fixed intact cells or tissue sections are hybridized with fluorescently labeled oligonucleotides complementary to 18S ribosomal RNA (rRNA) and viewed by fluorescent microscopy.

Bronchial lavage and induced sputum samples from *Pneumocystis carinii* positive human patients were concentrated to one-tenth of their original volume by centrifugation and 30 ul were smeared on clean glass slides. Lung tissue were touch-preped. The smears or tissue touch preps were air dried, fixed in 75% methanol and 25% glacial acetic acid for 10 minutes at room temperature and then air dried again. The samples were dehydrated through a series of ethanol (50% to 75% to 90% to 100%) soaks and then dried in air. Alternatively, if the tissue was already embedded in paraffin, it was treated with xylene (three 10 minutes treatments) to deparaffin the tissue. Excess xylene was removed by rinsing in 100% ethanol and air drying. One hundred microliters of probe hybridization mixture that contained 5 times SET (750 mM NaCl, 100 mM tris-HCl pH 7.8 and 5 mM EDTA), 0.2% bovine serum albumin (Sigma; fraction V), 10% dextran sulfate (Sigma; average molecular weight 50,000) and 1.7–2.0 ng/ul rhodamine-X labeled oligodeoxynucleotide probe 1486 was added to each slide. Oligonucleotide probes were rhodamine-X labeled according to DeLong et al. (Science 243:1660, 1989). Slides were covered with cover slips and incubated in a humid chamber at 60° C. for 16–18 hours. Coverslips were removed by immersion in 2×SET, and the slides were immediately washed three times in 0.2×SET at 60° C. for 10 minutes each time. Slides were dried in air and viewed immediately, or stored in the dark at 4° C. until ready to view them. Samples were mounted in ACCU.MOUNT 60 TM Mounting medium and viewed under oil immersion at 500×and 1,000×. Results of one such experiment with *Pneumocystis carinii* positive bronchial lavage sample and induced sputum sample show that *Pneumocystis carinii* specific rhodamine-X labeled probe 1486 hybridizes strongly only to *Pneumocystis carinii* in the bronchial lavage sample and induced sputum sample (indicated by bright red fluorescence). In other experiments with human, rat and ferret specimens, all probes behave in a fashion predicted by their hybridization patterns shown in Tables 2 and 3.

EXAMPLE 4

Inclusivity Analysis of probe hybridization behavior in liquid-hybridization assay.

The probes of the present invention or derivatives thereof could potentially be of significant value in a variety of hybridization formats. One such format, a dual probe, sandwich-type hybridization assay format (e.g. the homopolymer capture, dual probe, liquid hybridization format described in U.S. Ser. No. 277,579; U.S. Ser. No. 169,646, or U.S. Ser. No. 233,683), is used in this example. In such an application, an oligonucleotide probe generally is modified at its 3' terminus to contain a tract of deoxyadenosine (dA) residues ca. 20–200 residues long. This would be used to "capture" the target rRNA (following liquid hybridization) from the test sample onto a solid support (e.g., beads, plastic surface, filter, etc.) which had been suitably derivatized with polydeoxythymidine (dT) for this purpose. A second probe is used as a "detection" probe and would be derivatized by some detectable ligand (e.g. 32-P, fluorescien, biotin, etc.). In principle, the detection probe could be an oligonucleotide or a longer DNA or RNA probe. Detection of the presence of the target nucleic acid in a test sample then is indicated by the capture of the detection ligand onto the solid surface through the series of hybridization interactions:

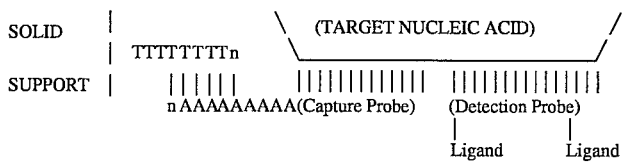

This could occur only if the target nucleic acid is present in the test sample. In principle, the above scheme could be employed with multiple capture and detection probes (probe sets) for the purpose of, for example, improving or enhancing sensitivity of the assay.

While the description of the invention has been made with reference to detecting rRNA, it will be readily understood that the probes described herein and probes complementary to those described herein also will be useful for the detection of the genes (DNA) which specify the rRNA and, accordingly, such probes are to be deemed equivalents to the described probes and encompassed within the spirit and scope to the present invention and the appended claims.

TABLE 1

PNEUMOCYSTIS CARINII 18S rRNA PROBES AND TARGET SEQUENCES

```
Pos. #              594                                                       628
                     |                                                         |
E. coli             GUUAAGUCAGAUGUGAAAUCCCCGGCUCAACCUGGAACUG                         E. coli
S. cerevi           UUGGGCCCGG–UUGCC–GGUCC–––GAUUUUUCGUGUACUG                         S. cerevi
P. carR             UAGGGAUUGG–UUGCCUGGUCC–UCCGAAGUGUGUGCACUG                         P. carR
P. carH8            –CGAU–GGUUGA–CGGCCCGGUc C–UCCGAAG–UGUGUGCACUG                     P. carH8
P. carF1            UAGGGAUUGG–UUACCCGGUCC–UCCGGAAAGGUGUGCACUG                        P. carF1
P. carF2            UAGGGUUGG–UUGCCUGGUCC–UCCGAAGUGUGUGCACUG                          P. carF2

Core Var.           AUUgg–uGgccCggucc–UCCGAAG–uGUgugc                                 Core Var.

Probe 1484          3' CCCCAACT–GCCGGGCCAGG–AGGCUUC–ACACACGc 5'                       Probe 1484
Probe 1493          3' CCCTAACC–AATGGGCCAGG–AGGCCUUUCCACACc 5'                        Probe 1493

Pos. #              641                                      (652)
                     |                                         |
E. coli             –U–ACUGGCAAGCU–––––––                                             E. coli
S. cerevi           ACGGGGCCUUCCCUUCUGG–CUAACC–UUGAGUCCCUU–G–UGG                      S. cerevi
P. carR             –UGAU–CCUUCCCUCUGG–AUUACC–GUAUGCCCUUCGCUGG                        P. carR
P. carH8            –CGAU–CCUUCCCUCUGGA–UUACCG–GUAUGCCCUUCAUUGG                       P. carH8
P. carF1            –CGAU–CCUUCCCUCUGGA–UUACCA–AUAUGCUCUUCAUUGG                       P. carF1
P. carF2            –UGAC–CCUUCUCCUGGAUUUACCA–GCAUGCCCUUCAUUGG                        P. carF2

Core Var.           gAY–ccuuCCUuCUGgA–UuACcG–GuAugCccuuc                              Core Var.

Probe 1497          3' CTA–GGAAGGAAGACCT–AATGGT–TATACGAGAAGc 5'                       Probe 1497
Probe 1496          3' CTG–GGAAGAAGGACCTAAATGT–CGTACGGGAAGc 5'                        Probe 1496
Probe 1485          3' CTA–GGAAGGAAGACCT–AATGGC–CATACGGAAGc 5'                        Probe 1485

Pos. #                                               (652)
                                                       |
E. coli             UUUUACUUUGAAAAAAAUUAGAGAGUUCAAAGCAGGCGUAUGCGUCGAAUAAUAUUA          E. coli
S. cerevi           AUUUUACUUUGAAAAUUAGAGAGUUCAAAGCAGGCGUUU–GCUCGAAUACAUUA             S. cerevi
P. carR             CUUUUACUUUGAGAAAAUUAGAGAGUUCAAAGCAGGCAUUU–gCUCGAAUAC–UUA           P. carR
P. carH8            CUUUUACUUUGAGAAAAUUAGAGAGUUCAAAGCAGGCAUUU–gCUCGAAUAC–UUA           P. carH8
P. carF1            GUUUUACUUUGAGAAAAUUAGAGAGUUCAAAGCAGGcGUUU–GCUCGa AUACAUUA          P. carF1
P. carF2            AUUUUACUUUGAGAAAAUUAGAGAGUUCAAAGCAGGCAUUU–GCUCGAAUACaUUA           P. carF2

Core Var.           tcuuugaGaaauuagaguguucaaagcaggcAuuu–gcucgaaua                     Core Var.

Probe 1159          3' TcTGAAACTCTTTTAATCTCACAAGTTTCGTCCGCAAA–CGAGCTTATc-5'           Probe 1159

Pos. #              1123                              1151
                     |                                 |
E. coli             CC–UUUGUUGCCAGCGGUC––––––––CGGCCG––GGAACUCAAAG–GAG                 E. coli
S. cerevi           CUACUAAAUAGUGGUGCUAGCAUUUGCUGUAUUGCCACUUCCUUAGAGGG                 S. cerevi
P. carR             CUGCUAAAUAGCCAGAUUAGCUUUGCUGAUCGCGGCCUUCUUAGAGGG                   P. carR
P. carH8            CUGCUAAAUAGCCAGAUUAGCUUUGCUGAUCGCAGCCUUCUUAGAGGG                   P. carH8
P. carF1            CUGCUAAAUAGCCAGAUUAGCUUUGCUGAUCGCUGAGCCUUCUUAGAGGG                 P. carF1
P. carF2            CUGCUAAAUAGCCAGAUUAGCUUUUGCUGAUCGCCGGCCUUCUUAGAGGG                 P. carF2
```

TABLE 1-continued

PNEUMOCYSTIS CARINII 18S rRNA PROBES AND TARGET SEQUENCES

| Core Var. | CCAGAUu Ag c Uuuugcug Auc g c AGGc u u c u u | Core Var. |
|---|---|---|
| Probe 1162 | 3'Tc TTTATCGGTCTAATCGAAAACGACTAGCGCCCGAAGAAc -5' | Probe 1162 |
| Probe 1492 | 3'GGTCTAATCGT AAGCGACTAGCGTCCGAAGAATc 5' | Probe 1492 |
| Probe 1486 | 3'GGTCTAATCGAAAACGACTAGCGTCCGAAGAATc 5' | Probe 1486 |

| Pos. # | (1451) | 1481 | |
|---|---|---|---|
| | 1436 | | |
| E. coli | GAAGUAGGUAGCUU- AACCUU- — — — — — — — — — — — — — — — — CGGGAGGGCGCUUACCACUUGUGAUUCAUGACUG | E. coli |
| S. cerevi | GUGAGGCCUCAGGAUCUGCUUAGAGAAGGGGCAACUCCAU—CUCAGAGCGAGAAUUUGGACAAACUUGGUCAUUUAGAGGA | S. cerevi |
| P. carR | AUGAGGUCUUCGGACUGGUGAUGGGUAUUGGCAACGAUAAGCCUAUUACUGGAAAGUUGAUCAAa u n UGg u c a u u u AGAg g A | P. carR |
| P. carH6 | GUGAGGUCUUCGGACUGGCAGUGGGCUGUUGGCAACGAUGA–CCCAUGUCUGGAAAGUUGa u CAAAUUGGUCAUUU.... | P. carH6 |
| P. carH8 | GUGAGGUCUUCGGACUGGNAGCGGGCUGUUGGNAANNAUGA–NCCAUUGCUGg AAA.... | P. carH8 |
| P. carF1 | GUGAGGUCUUCGGACCGGU–AAUGGCAUUGGUUUCGAUGU–UCCGUUGCUGGAAAGUUGANUAAAAUUGGUCA.... | P. carF1 |
| P. carF2 | GUGAGGu c UUCGGACUGGCGAUGGGCCAUUGGUAACGAUGG–CCUGUUGCUGGAAAGUUGAUCAAAUUUGGUCAUUUAGA... | P. carR |

| Core Var. | u u Cg g a CUGg CAGYg Gg CUGUUg g c a a c GAUGAc Cc aauucGUgGAaaGuuuGaUcaaaUuuugucauuu | Core Var. |
|---|---|---|
| Probe 1487 | 3' AAGCCTGACCGTCGCCCGACAACCGTTGCTACT-Gc 5' | Probe 1487 |
| Probe 1495 | 3' AAGCCTGACCGCTACCCGGTAACCATTGCTACC–Gc 5' | Probe 1495 |
| Probe 1994 | 3' AAGCCTGCCA–TTACCAGTAACCAAAGCTACA–AGc 5' | Probe 1994 |
| Probe 1488 | 3'GGTAACGACCTTTCAACTAGTTTAAACCAGTAAc -5' | Probe 1488 |
| Probe 1491 | 3'GACAACGACCTTTCAACTAGTTTAAACCAGTAAc 5' | Probe 1491 |

"Core" region of variation: upper case letters indicate most important positions of nucleotide sequence variation between the human *Pneumocystis carinii* 18S rRNA sequence and that of *Saccharomyces cerevisiae*. Probe inclusivity and exclusivity behavior rely heavily upon the use of these position. E. coli = *Escherichia coli*; P. car = *Pneumocystis carinii*; S. cerevi = *Saccharomyces cerevisiae*; F1 and F2 = ferret; H6 and H8 = human; and R = rat.

TABLE 2

PNEUMOCYSTIS CARINII INCLUSIVITY-PANEL (SOUTHERN-BLOT DATA)

| SAMPLES (a) | PROBE HYBRIDIZATION | | | | | | | |
|---|---|---|---|---|---|---|---|---|
| | 1484 H | 1497 F | 1485 H | 1493 F | 1496 F | 1486 H | 1162 R | 1492 F |
| Human PC 1 (A) | ++++ | − | ++++ | − | ++ | ++++ | +++ | ++ |
| Human PC 2 (A) | ++++ | − | ++++ | − | ++ | ++++ | +++ | ++ |
| Human PC 3 (A) | ++++ | − | ++++ | − | ++ | ++++ | +++ | ++ |
| Human PC 4 (A) | ++++ | − | ++++ | − | ++ | ++++ | +++ | ++ |
| Human PC 6 (A) | ++++ | − | ++++ | − | ++ | ++++ | +++ | ++ |
| Ferret PC 71 | ++++ | − | + | − | ++++ | ++++ | ++++ | − |
| Ferret PC 101 | ++ | ++++ | + | +++ | + | ++++ | ++ | +++ |
| Ferret PC 104 | + | + | + | ++++ | + | ++++ | ++ | +++ |
| Ferret PC RNA | ++++ | +++ | − | ++++ | + | ++++ | ++ | +++ |
| Rat PC RNA | ++ | − | − | ++ | − | ++++ | ++++ | ++++ |

| SAMPLES (a) | PROBE HYBRIDIZATION | | | | | |
|---|---|---|---|---|---|---|
| | 1487 H | 1495 F | 1491 F | 1488 H | 1494 F | 1159 H |
| Human PC 1 (A) | ++++ | − | +++ | ++++ | − | ++++ |
| Human PC 2 (A) | ++++ | − | +++ | ++++ | − | ++++ |
| Human PC 3 (A) | ++++ | − | ++++ | ++++ | − | ++++ |
| Human PC 4 (A) | ++++ | − | ++++ | ++++ | − | ++++ |
| Human PC 6 (A) | ++++ | − | ++ | ++++ | − | ++++ |
| Ferret PC 71 | + | ++++ | ++++ | ++++ | + | ++++ |
| Ferret PC 101 | + | − | ++++ | ++++ | ++++ | ++++ |
| Ferret PC 104 | + | − | ++++ | + | − | ++++ |
| Ferret PC RNA | + | +++ | ++++ | ++ | + | ++++ |
| Rat PC RNA | + | ++ | ++++ | ++++ | ++ | ++++ |

++++ = positive control level of hybridization,
+ = barely detectable and
− = zero.
Human PC (A) = PCR Amplified 18S rDNA;
Ferret PC = cloned 18S genes;
PC RNA = RNA prepared from heavily infected samples.
RNA from infected lung tissue of ferret and rat analysed by dot-blot hybridization.

TABLE 3

DOT-BLOT HYBRIDIZATION OF 18S rRNA-TARGETED PROBES

| Strain | Genus species | 1484 H | 1497 F | 1485 H | 1493 F | 1496 F | 1486 H | 1162 F | 1492 F | 1487 H | 1495 F | 1488 H | 1494 F | 1491 F | 1159 H |
|---|---|---|---|---|---|---|---|---|---|---|---|---|---|---|---|
| GT803 | Human P. carinii 1 (BW) | +++ | - | +++ | - | - | +++ | +++ | - | +++ | - | +++ | - | +++ | +++ |
| GT008 | Bacillus brevis | - | - | - | - | - | - | - | - | - | - | - | - | - | - |
| GT811 | Bacillus cereus | - | - | - | - | - | - | - | - | - | - | - | - | - | - |
| GT804 | Bacillus coagulans | - | - | - | - | - | - | - | - | - | - | - | - | - | - |
| GT0010 | Bacillus subtilis | - | - | - | - | - | - | - | - | - | - | - | - | - | - |
| GT0011 | Bacteroides fragilis | - | - | - | - | - | - | - | - | - | - | - | - | - | - |
| GT0012 | Bacteroides melaninogenicus | - | - | - | - | - | - | - | - | - | - | - | - | - | - |
| GT0013 | Bifidobacterium dentium | - | - | - | - | - | - | - | - | - | - | - | - | - | - |
| GT0030 | Bordetella bronchiseptica | - | - | - | - | - | - | - | - | - | - | - | - | - | - |
| IG0687 | Citrobacter diversus | - | - | - | - | - | - | - | - | - | - | - | - | - | - |
| GT0045 | Citrobacter freundii | - | - | - | - | - | - | - | - | - | - | - | - | - | - |
| PB | Corynebacterium genitalium | - | - | - | - | - | - | - | - | - | - | - | - | - | - |
| GT0686 | Enterobacter agglomerans | - | - | - | - | - | - | - | - | - | - | - | - | - | - |
| GT0237 | Enterobacter cloacae | - | - | - | - | - | - | - | - | - | - | - | - | - | - |
| GT0238 | Flavobacterium meningosepticum | - | - | - | - | - | - | - | - | - | - | - | - | - | - |
| GT241 | Fusobacterium necrophorum | - | - | - | - | - | - | - | - | - | - | - | - | - | - |
| GT0244 | Hafnia alvei | - | - | - | - | - | - | - | - | - | - | - | - | - | - |
| 41Y | Haemophilus influenzas | - | - | - | - | - | - | - | - | - | - | - | - | - | - |
| GT1500 | Klebsiella oxytoca | - | - | - | - | - | - | - | - | - | - | - | - | - | - |
| GT3194 | Klebsiella pneumonoia | - | - | - | - | - | - | - | - | - | - | - | - | - | - |
| ATCC3340 | Kurthia zopfii | - | - | - | - | - | - | - | - | - | - | - | - | - | - |
| GT256 | Lactobacillus acidophilus | - | - | - | - | - | - | - | - | - | - | - | - | - | - |
| IG3344 | Listeria monocytogenes | - | + | - | - | - | - | - | - | - | - | + | - | - | - |
| IG3194 | Listeria monocytogenes | - | + | - | - | - | - | - | - | - | - | + | - | - | - |
| ATCC401 | Micrococcus conoglomeratus | - | - | - | - | - | - | - | - | - | - | - | - | - | - |
| ATCC381 | Micrococcus luteus | - | - | - | - | - | - | - | - | - | - | - | - | - | - |
| GT298 | Micrococcus sp. | - | - | - | - | - | - | - | - | - | - | - | - | - | - |
| GT299 | Micrococcus sp. | - | - | - | - | - | - | - | - | - | - | - | - | - | - |
| | Mycobacterium avium | - | - | - | - | - | - | - | - | - | - | - | - | - | - |
| | Mycobacterium bovis | - | - | - | - | - | - | - | - | - | - | - | - | - | - |
| | Mycobacterium fortuitum | - | - | - | - | - | - | - | - | - | - | - | - | - | - |
| | Mycobacterium kansasii | - | - | - | - | - | - | - | - | - | - | - | - | - | - |
| GT0307 | Neisseria cinerea | - | - | - | - | - | - | - | - | - | - | - | - | - | - |
| CT0310 | Neisseria flavescens | - | - | - | - | - | - | - | - | - | - | - | - | - | - |
| GT0135 | Neisseria gonorrhoeae | - | - | - | - | - | - | - | - | - | - | - | - | - | - |
| GT0347 | Neisseria lactamica | - | - | - | - | - | - | - | - | - | - | - | - | - | - |
| GT0350 | Neisseria meningitidis | - | - | - | - | - | - | - | - | - | - | - | - | - | - |
| GT0353 | Neisseria mucosa | - | - | - | - | - | - | - | - | - | - | - | - | - | - |
| GT0355 | Neisseria sicca | - | - | - | - | - | - | - | - | - | - | - | - | - | - |
| GT0356 | Neisseria subflava | - | - | - | - | - | - | - | - | - | - | - | - | - | - |
| GT0358 | Pasteurella multocida | - | - | - | - | - | - | - | - | - | - | - | - | - | - |
| GT0360 | Peptococcus anaerobius | - | - | - | - | - | - | - | - | - | - | - | - | - | - |
| GT1918 | Pseudomonas putida | - | - | - | - | - | - | - | - | - | - | - | - | - | - |
| GT2024 | Pseudomonas picketii | - | - | - | - | - | - | - | - | - | - | - | - | - | - |

TABLE 3-continued

DOT-BLOT HYBRIDIZATION OF 18S rRNA-TARGETED PROBES

| Strain | Genus species | 1484 H | 1497 F | 1485 H | 1493 F | 1496 F | 1486 H | 1162 F | 1492 F | 1487 H | 1495 F | 1488 H | 1494 F | 1491 F | 1159 H |
|---|---|---|---|---|---|---|---|---|---|---|---|---|---|---|---|
| e23566 | *Salmonella typhimurium* | — | — | — | — | — | — | — | — | — | — | — | — | — | — |
| RF910 | *Salmonella arizonae* | — | — | — | — | — | — | — | — | — | — | — | — | — | — |
| RF968 | *Shigella sonnei* | — | — | — | — | — | — | — | — | — | — | — | — | — | — |
| RF970 | *Shigella dysenteriae* | — | — | — | — | — | — | — | — | — | — | — | — | — | — |
| RF974 | *Shigella boydii* C13 | — | — | — | — | — | — | — | — | — | — | — | — | — | — |
| ATCC6473 | *Sporosarcina ureae* | — | — | — | — | — | — | — | — | — | — | — | — | — | — |
| ATCC13881 | *Sporosarcina ureae* | — | — | — | — | — | — | — | — | — | — | — | — | — | — |
| GT399 | *Staphylococcus aureus* | — | — | — | — | — | — | — | — | — | — | + | — | — | — |
| GT1366 | *Staphylococcus aureus* | — | — | — | — | — | — | — | — | — | — | + | — | — | — |
| GT1711 | *Staphylococcus aureus* | — | — | — | — | — | — | — | — | — | — | + | — | — | — |
| ATCC8095 | *Staphylococcus aureus* | — | — | — | — | — | — | — | — | — | — | + | — | — | — |
| ATCC12598 | *Staphylococcus aureus* | — | — | — | — | — | — | — | — | — | — | + | — | — | — |
| ATCC13565 | *Staphylococcus aureus* | — | — | — | — | — | — | — | — | — | — | + | — | — | — |
| ATCC27154 | *Staphylococcus aureus* | — | — | — | — | — | — | — | — | — | — | + | — | — | — |
| ATCC27659 | *Staphylococcus aureus* | — | — | — | — | — | — | — | — | — | — | + | — | — | — |
| ATCC27660 | *Staphylococcus aureus* | — | — | — | — | — | — | — | — | — | — | + | — | — | — |
| ATCC27690 | *Staphylococcus aureus* | — | — | — | — | — | — | — | — | — | — | + | — | — | — |
| ATCC33753 | *Staphylococcus auricularis* | — | — | — | — | — | — | — | — | — | — | — | — | — | — |
| ATCC27840 | *Staphylococcus capitis* | — | — | — | — | — | — | — | — | — | — | — | — | — | — |
| ATCC13548 | *Staphylococcus caseolyticus* | — | — | — | — | — | — | — | — | — | — | — | — | — | — |
| GT401 | *Staphylococcus epidermidis* | — | — | — | — | — | — | — | — | — | — | — | — | — | — |
| GT402 | *Staphylococcus epidermidis* | — | — | — | — | — | — | — | — | — | — | — | — | — | — |
| CT403 | *Staphylococcus epidermidis* | — | — | — | — | — | — | — | — | — | — | — | — | — | — |
| ATCC155 | *Staphylococcus epidermidis* | — | — | — | — | — | — | — | — | — | — | — | — | — | — |
| ATCC29885 | *Staphylococcus haemolyticus* | — | — | — | — | — | — | — | — | — | — | — | — | — | — |
| GT1162 | *Staphylococcus haemolyticus* | — | — | — | — | — | — | — | — | — | — | — | — | — | — |
| ATCC29970 | *Staphylococcus hominis* | — | — | — | — | — | — | — | — | — | — | — | — | — | — |
| GT667 | *Staphylococcus hominis* | — | — | — | — | — | — | — | — | — | — | — | — | — | — |
| GT1752 | *Staphylococcus hominis* | — | — | — | — | — | — | — | — | — | — | — | — | — | — |
| GT1875 | *Staphylococcus intermedius* | — | — | — | — | — | — | — | — | — | — | — | — | — | — |
| ATCC29663 | *Staphylococcus lentus* | — | — | — | — | — | — | — | — | — | — | — | — | — | — |
| ATCC29070 | *Staphylococcus saprophyticus* | — | — | — | — | — | — | — | — | — | — | — | — | — | — |
| GT404 | *Staphylococcus saprophyticus* | — | — | — | — | — | — | — | — | — | — | — | — | — | — |
| GT1809 | *Staphylococcus saprophyticus* | — | — | — | — | — | — | — | — | — | — | — | — | — | — |
| ATCC35552 | *Staphylococcus* sci. sub. sci. | — | — | — | — | — | — | — | — | — | — | — | — | — | — |
| ATCC29060 | *Staphylococcus* sci. sub. sci. | — | — | — | — | — | — | — | — | — | — | — | — | — | — |
| ATCC29062 | *Staphylococcus simulans* | — | — | — | — | — | — | — | — | — | — | — | — | — | — |
| ATCC27848 | *Staphylococcus warneri* | — | — | — | — | — | — | — | — | — | — | — | — | — | — |
| ATCC27836 | *Staphylococcus xylosus* | — | — | — | — | — | — | — | — | — | — | — | — | — | — |
| ATCC29971 | *Streptococcus agalactiae* | — | — | — | — | — | — | — | — | — | — | — | — | — | — |
| GT405 | *Streptococcus faecalis* | — | — | — | — | — | — | — | — | — | — | — | — | — | — |
| GT1668 | *Streptococcus bovis* | — | — | — | — | — | — | — | — | — | — | — | — | — | — |
| GT406 | *Streptococcus mutans* | — | — | — | — | — | — | — | — | — | — | — | — | — | — |
| DAC | *Streptococcus faecium* | — | — | — | — | — | — | — | — | — | — | — | — | — | — |
| GT668 | | — | — | — | — | — | — | — | — | — | — | — | — | — | — |

TABLE 3-continued

DOT-BLOT HYBRIDIZATION OF 18S rRNA-TARGETED PROBES

| | | PROBE HYBRIDIZATION | | | | | | | | | | | | | |
|---|---|---|---|---|---|---|---|---|---|---|---|---|---|---|---|
| Strain | Genus species | 1484 H | 1497 F | 1485 H | 1493 F | 1496 F | 1486 H | 1162 F | 1492 F | 1487 H | 1495 F | 1488 H | 1494 F | 1491 F | 1159 H |
| GT408 | *Streptococcus pneumoniae* | — | — | — | — | — | — | — | — | — | — | — | — | — | — |
| GT410 | *Streptococcus salivarius* | — | — | — | — | — | — | — | — | — | — | — | — | — | — |
| GT411 | *Streptococcus sanguis* | — | — | — | — | — | — | — | — | — | — | — | — | — | — |
| ATCC36607 | *Aspergillus fumigatus* (c) | — | — | — | — | — | — | — | — | — | — | — | — | — | ++++ |
| 5829 | *Aspergillus brunnescens* | — | — | — | — | — | — | — | — | — | — | — | — | — | ++++ |
| ATCC10124 | *Aspergillus flavus* | — | — | — | — | — | — | — | — | — | — | — | — | — | ++++ |
| ATCC10074 | *Aspergillus nidulans* | — | — | — | — | — | — | — | — | — | — | — | — | — | ++++ |
| ATCC16888 | *Aspergillus niger* | — | — | — | — | — | — | — | — | — | — | — | — | — | ++++ |
| ATCC15517 | *Aspergillus parasiticus* | — | — | — | — | — | — | — | — | — | — | — | — | — | ++++ |
| ATCC46941 | *Aspergillus terreus* | — | — | — | — | — | — | — | — | — | — | — | — | — | ++++ |
| ATCC 9577 | *Aspergillus versicolor* | — | — | — | — | — | — | — | — | — | — | — | — | — | ++++ |
| ATCC60916 | *Blastomyces dermatitidis* | — | — | — | — | — | — | — | — | — | — | — | — | — | ++++ |
| ATCC11006 | *Candida albicans* | — | — | — | — | — | — | — | — | — | — | — | — | — | ++++ |
| ATCC14053 | *Candida albicans* | — | — | — | — | — | — | — | — | — | — | — | — | — | ++++ |
| ATCC18804 | *Candida albicans* | — | — | — | — | — | — | — | — | — | — | — | — | — | ++++ |
| ATCC24433 | *Candida albicans* | — | — | — | — | — | — | — | — | — | — | — | — | — | ++++ |
| ATCC36232 | *Candida albicans* | — | — | — | — | — | — | — | — | — | — | — | — | — | ++++ |
| ATCC60193 | *Candida albicans* | — | — | — | — | — | — | — | — | — | — | — | — | — | ++++ |
| 190-87 | *Candida albicans* (sp) | — | — | — | — | — | — | — | — | — | — | — | — | — | ++++ |
| 266-87 | *Candida albicans* (bw) | — | — | — | — | — | — | — | — | — | — | — | — | — | ++++ |
| ATCC6260 | *Candida guilliermondii* | — | — | — | — | — | — | — | — | — | — | — | — | — | ++++ |
| ATCC4135 | *Candida kefyr* | — | — | — | — | — | — | — | — | — | — | — | — | — | ++++ |
| ATCC46764 | *Candida kefyr* | — | — | — | — | — | — | — | — | — | — | — | — | — | +++ |
| ATCC6258 | *Candida krusei* | — | — | — | — | — | — | — | — | — | — | — | — | — | — |
| 46-87 | *Candida krusei* (sp) | — | — | — | — | — | — | — | — | — | — | — | — | — | ± |
| 528-87 | *Candida krusei* (sp) | — | — | — | — | — | — | — | — | — | — | — | — | — | + |
| 0565-84 | *Candida lipolytica* (sp) | — | — | — | — | — | — | — | — | — | — | — | — | — | ++++ |
| 1034-86 | *Candida lipolytica* (bw) | — | — | — | — | — | — | — | — | — | — | — | — | — | ++++ |
| ATCC42720 | *Candida lusitaniae* | — | — | — | — | — | — | — | — | — | — | — | — | — | — |
| 1215-85 | *Candida lusitaniae* (bw) | — | — | — | — | — | — | — | — | — | — | — | — | — | — |
| 150-87 | *Candida lusitaniae* (sp) | — | — | — | — | — | — | — | — | — | — | — | — | — | — |
| 964-88 | *Candida parapsilosis* | — | — | — | — | — | — | — | — | — | — | — | — | — | ++++ |
| ATCC22019 | *Candida parapsilosis* | — | — | — | — | — | — | — | — | — | — | — | — | — | ++++ |
| 0914-86 | *Candida pseudotropicalis* (bw) | — | — | — | — | — | — | — | — | — | — | — | — | — | ++++ |
| 999-88 | *Candida pseudotropicalis* (bw) | — | — | — | — | — | — | — | — | — | — | — | — | — | — |
| ATCC58964 | *Candida rugosa* | — | — | — | — | — | — | — | — | — | — | — | — | — | — |
| ATCC750 | *Candida tropicalis* | — | — | — | — | — | — | — | — | — | — | — | — | — | ++++ |
| ATCC13803 | *Candida tropicalis* | — | — | — | — | — | — | — | — | — | — | — | — | — | ++++ |
| ATCC42678 | *Candida tropicalis* | — | — | — | — | — | — | — | — | — | — | — | — | — | ++++ |
| 150-87 | *Candida tropicalis* (sp) | — | — | — | — | — | — | — | — | — | — | — | — | — | ++++ |
| 802-88 | *Candida tropicalis* (bw) | — | — | — | — | — | — | — | — | — | — | — | — | — | ++++ |
| ATCC9226 | *Candida utilis* | — | — | — | — | — | — | — | — | — | — | — | — | — | ++++ |
| ATCC22981 | *Candida viswanathii* | — | — | — | — | — | — | — | — | — | — | — | — | — | ++++ |
| ATCC14116 | *Cryptococcus neoformans* | — | — | — | — | — | — | — | — | — | — | — | — | — | ++++ |
| ATCC32045 | *Cryptococcus neoformans* | — | — | — | — | — | — | — | — | — | — | — | — | — | ++++ |
| ATCC12700 | *Histoplasma capsulatum* | — | — | — | — | — | — | — | — | — | — | — | — | — | +++ |

TABLE 3-continued

DOT-BLOT HYBRIDIZATION OF 18S rRNA-TARGETED PROBES

PROBE HYBRIDIZATION

| Strain | Genus species | 1484 H | 1497 F | 1485 H | 1493 F | 1496 F | 1486 H | 1162 F | 1492 F | 1487 H | 1495 F | 1488 H | 1494 F | 1491 F | 1159 H |
|---|---|---|---|---|---|---|---|---|---|---|---|---|---|---|---|
| ATCC14692 | *Neurospora crassa* | - | - | - | - | - | - | - | - | - | - | - | - | - | - |
| ATCC48093 | *Paracoccidioides brasiliensis* | - | - | - | - | - | - | - | - | - | - | - | - | - | +++ |
| ATCC10106 | *Pen. chrysogenum* | - | - | - | - | - | - | - | - | - | - | - | - | - | +++ |
| ATCC9179 | *Pen. notatum* | - | - | - | - | - | - | - | - | - | - | - | - | - | +++ |
| ATCC28169 | *Pseudallescheria boydii* | - | - | - | - | - | - | - | - | - | - | - | - | - | - |
| ATCC22959 | *Rhizopus oligosporus* | - | - | - | - | - | - | - | - | - | - | - | - | - | - |
| ATCC10788 | *Rhod. toruloides* | - | - | - | - | - | - | - | - | - | - | - | - | - | +++ |
| ATCC18824 | *Saccharomyces cerevisiae* | - | - | - | - | - | - | - | - | - | - | - | - | - | +++ |
| ATCC14284 | *Sporothrix schenkii* | - | - | - | - | - | - | - | - | - | - | - | - | - | - |
| ATCC2001 | *Torulopsis glabrata* | - | - | - | - | - | - | - | - | - | - | - | - | - | +++ |
| 275-87 | *Torulopsis glabrata* (sp) | - | - | - | - | - | - | - | - | - | - | - | - | - | +++ |
| 359-87 | *Torulopsis glabrata* (bw) | - | - | - | - | - | - | - | - | - | - | - | - | - | +++ |
| ATCC28592 | *Trich. beigelii* | - | - | - | - | - | - | - | - | - | - | - | - | - | ++ |
| j1402 | *Ustilago maydis* | - | - | - | - | - | - | - | - | - | - | - | - | - | - |
| ATCC18942 | *Yarrowia lipolytica* | - | - | - | - | - | - | - | - | - | - | - | - | - | + |
| | CaSki cells RNA | - | - | - | - | - | - | - | - | - | - | - | - | - | - |
| | Wheat Germ RNA | | | | | | | | | | | | | | |
| | Ferret PC + ve RNA | +++ | - | - | +++ | - | +++ | ++ | +++ | + | +++ | +++ | ++ | +++ | +++ |
| | Rat PC + ve RNA | ++ | +++ | - | ++ | - | +++ | +++ | +++ | + | ++ | +++ | - | +++ | +++ |

Exclusivity data was determined after overnight exposure. Each organism is represented by 100 ng of CsTFA purified RNA.
+++ = positive control level of hybridization,
+ = barely detectable,
- = zero.
BW = organism isolated from bronchial lavage sample and
SP = organism isolated from sputum sample.
PC = *Pneumocystis carinii*

What is claimed is:

1. A nucleic acid fragment to be used as a probe for detecting human *Pneumocystis carinii* in a hybridization assay, wherein said fragment consists essentially of a sequence that is selected from at least thirteen consecutive nucleotides of probe 1485 or the full length complementary sequence thereof.

2. The nucleic acid fragment of claim 1, wherein said fragment consists essentially of a sequence that is selected from at least fifteen consecutive nucleotides of probe 1485 or the full length complementary sequence thereof.

3. The nucleic acid fragment of claim 2, wherein said fragment consists essentially of a sequence that is selected from at least twenty consecutive nucleotides of probe 1485 or the full length complementary sequence thereof.

4. The nucleic acid fragment of claim 3, wherein said fragment consists essentially of the entire sequence of probe 1485 or its full length complementary sequence.

5. A nucleic acid fragment to be used as a probe for detecting human *Pneumocystis carinii* in a hybridization assay, wherein said fragment consists essentially of a sequence that is selected from at least thirteen consecutive nucleotides of probe 1487 or the full length complementary sequence thereof.

6. The nucleic acid fragment of claim 5, wherein said fragment consists essentially of a sequence that is selected from at least fifteen consecutive nucleotides of probe 1487 or the full length complementary sequence thereof.

7. A nucleic acid fragment of claim 6, wherein said fragment consists essentially of a sequence that is selected from at least twenty consecutive nucleotides of probe 1487 or the full length complementary sequence thereof.

8. The nucleic acid fragment of claim 7, wherein said fragment consists essentially of the entire sequence of probe 1487 or its full length complementary sequence.

9. A nucleic acid fragment to be used as a probe for detecting human *Pneumocystis carinii* in a hybridization assay, wherein said fragment consists essentially of a sequence that is selected from at least thirteen consecutive nucleotides of probe 1159 or the full length complementary sequence thereof.

10. The nucleic acid fragment of claim 9, wherein said fragment consists essentially of a sequence that is selected from at least fifteen consecutive nucleotides of probe 1159 or the full length complementary sequence thereof.

11. A nucleic acid fragment of claim 10, wherein said fragment consists essentially of a sequence that is selected from at least twenty consecutive nucleotides of probe 1159 or the full length complementary sequence thereof.

12. The nucleic acid fragment of claim 11, wherein said fragment consists essentially of the entire sequence of probe 1159 or its full length complementary sequence.

* * * * *